United States Patent [19]

Makin

[11] Patent Number: 4,686,354

[45] Date of Patent: Aug. 11, 1987

[54] INHALATION APPARATUS

[75] Inventor: Ronald P. Makin, Skipton, United Kingdom

[73] Assignee: The BOC Group plc, Windlesham, England

[21] Appl. No.: 846,437

[22] Filed: Mar. 31, 1986

[30] Foreign Application Priority Data

Apr. 4, 1985 [GB] United Kingdom ................. 8508921

[51] Int. Cl.[4] ............................................ A61M 16/16

[52] U.S. Cl. ............................... 219/301; 128/204.17; 138/103; 219/272; 219/535; 219/549

[58] Field of Search .......................... 138/103; 174/47; 219/301, 271, 272, 535, 544, 548, 549; 128/203.17, 203.27, 204.17

[56] References Cited

U.S. PATENT DOCUMENTS

| | | | |
|---|---|---|---|
| Re. 29,332 | 8/1977 | Bilbro et al. | 138/103 X |
| 2,602,608 | 7/1952 | Darling | 174/47 X |
| 2,846,560 | 8/1958 | Jacoby et al. | 219/549 X |
| 3,275,803 | 9/1966 | True | 174/47 X |
| 4,038,519 | 7/1977 | Foucras | 219/301 |
| 4,553,023 | 11/1985 | Jameson et al. | 219/301 |

FOREIGN PATENT DOCUMENTS

| | | |
|---|---|---|
| 897292 | 5/1962 | United Kingdom . |
| 1448473 | 9/1976 | United Kingdom . |

*Primary Examiner*—Stephen Marcus
*Assistant Examiner*—Mark Thronson
*Attorney, Agent, or Firm*—Roger M. Rathbun; Larry R. Cassett

[57] ABSTRACT

A composite flexible delivery hose 1 for use with a medical humidifier comprises an inner tubular member 2 around which is spirally wound a heater cable 4. The heater cable 4 includes an outer body 6 of electrically insulating material in which is embedded an electrical resistance heater wire 8, a wire 10 interconnecting temperature sensors arranged one at each end of the hose and a thermoplastic support wire 12.

1 Claim, 4 Drawing Figures

16
2
1
4
14

INHALATION APPARATUS

BACKGROUND OF THE INVENTION

The present invention relates to delivery hoses for the passage therethrough of gases and in particular to delivery hoses associated with medical humidifiers.

It has long been appreciated that, when the upper airway of a patient is by-passed for prolonged periods by, for example, an endotracheal tube, it is important that means for the adequate humidification of the gas inhaled by the patient be provided. Such a humidification means is disclosed in U.K. Pat. No. 1448473. This document refers to a particular problem associated with medical humidifiers, namely the problem of "rain-out". Considerable heat losses can occur during the passage of a humidified gas when it leaves the humidifying chamber and passes along a delivery hose towards the patient. Such heat losses can result in condensation of water taking place inside the delivery hose with subsequent danger to the patient.

In order to overcome the problem of "rain-out", UK Pat. No. 1448473 teaches the use of a linear electrical resistance heater which is provided along the delivery hose and whose heat dissipation is controlled independently of the temperature of the water in the humidifying chamber. Associated with the heater is a temperature sensor situated at the delivery end of hose and a delivery control unit.

There are two problems associated with this known delivery hose. Firstly, the linear electrical resistance wire, together with the sensor renders the hose cumbersome. Secondly, since the sensor is thermally isolated from the heater, it relies on gas flow to indicate the gas temperature. If there is a period in which no gas flows, then the temperature of the gas at the sensor starts to fall and the control unit responds to this fall by increasing the power to the heater. This results in the system heading towards its maximum operating temperature. When the gas flow is turned on again, a transient temperature overshoot occurs.

U.K. Pat. No. 897292 describes an electrically heated flexible hose in which a fabric tape is wound helically around a flexible inner core. Mounted on the tape is a heating wire which is secured to the tape either by being interwoven therewith or by stitching. The heating wire is relatively exposed which necessitates the use of a lagging of heat insulating material which is surrounded by a protective covering. All this renders the hose cumbersome and therefore unsuitable for use in medical applications.

SUMMARY OF THE INVENTION

It is an aim of the present invention to provide a delivery hose for use with a medical humidifier which minimises the problems referred to above and permits the medical humidifier to be controlled to safe operating temperatures during a period of no gas flow.

According to the present invention, a composite, flexible delivery hose for use with a medical humidifier comprises an inner flexible tubular member, a heater cable attached to and wound spirally around the tubular member, the heater cable including an outer body of electrically insulating material in which is embedded an electrical resistance heater wire.

BRIEF DESCRIPTION OF DRAWINGS

An embodiment of the invention will now be described by way of example, reference being made to the Figures of the accompanying diagrammatic drawings, in which.

DESCRIPTION OF PREFERRED EMBODIMENT

Figure 1:
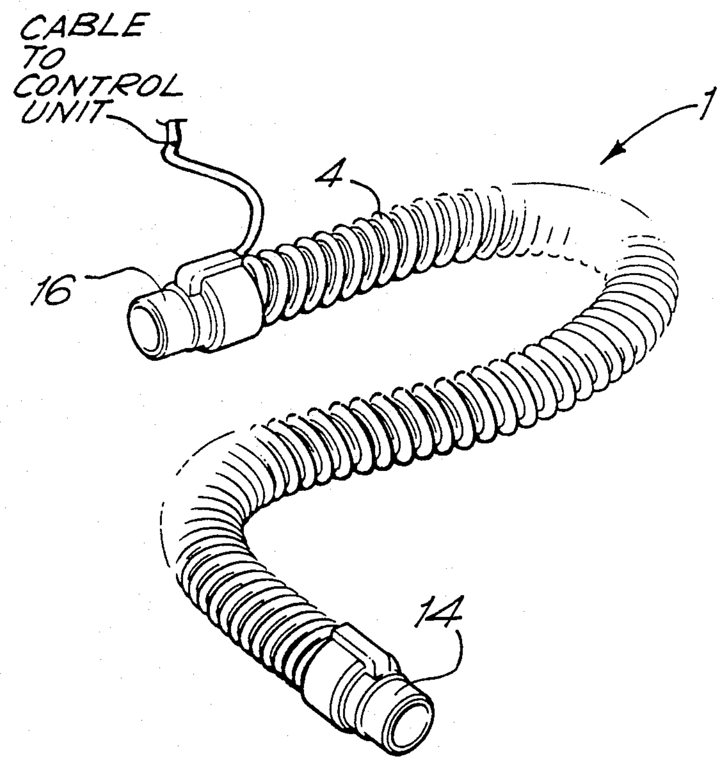
FIG. 1 is a perspective view of a composite flexible delivery hose.
Figure 2:
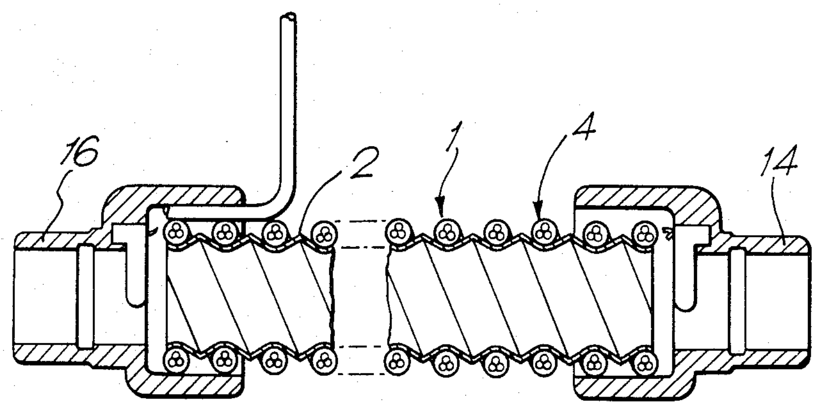
FIG. 2 is a longitudinal cross-section through the delivery hose of FIG. 1.
Figure 3:
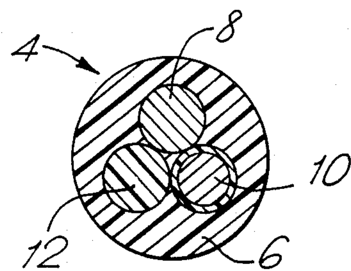
FIG. 3 is a transverse cross-section of a heater cable forming part of the delivery hose of FIGS. 1 and 2.

As shown, a composite, flexible delivery hose 1 for connection to the outlet of a medical humidifier comprises an inner, flexible tubular member 2 and a heater cable 4 wound spirally therearound. The tubular member 2 may be made from silicon rubber.

The heater cable 4 comprises an outer body 6 of electrically insulating material, for example, silicon rubber in which is embedded an uninsulated electrical resistance heater wire 8, a silicon covered wire 10 and a thermoplastic support wire 12. The heater cable 4 can be attached to the tubular member 2 by, for example, adhesion, or vulcanisation.

Figure 4:
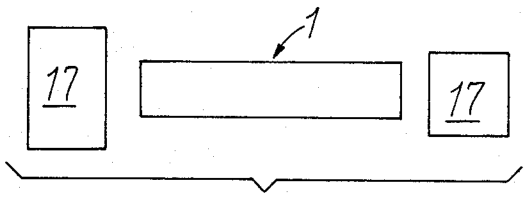
FIG. 4 is a schematic depiction of the preferred embodiment.

The silicon covered wire 10 interconnects two temperature sensors (17, FIG. 4) arranged one at each end of the hose 1.

It will be apparent that heat emanating from the wire 8 is evenly distributed along the length of the delivery hose 1.

The support wire 12 ensures that the hose 1 maintains its profile during flexing and recovers from accidental crushing.

The materials for the tubular member 2 and the outer body 6 are selected to allow standard means of sterilisation, for example, autoclaving, thereby making the delivery hose reusable.

It has been found that, by using a heater wire 8 spiralled around the inner tubular member 2, the effect of transient temperature overshoot is minimised. It has also been found that the hose temperature need only be maintained at approximately 2° C. above gas temperature to maintain the gas at the temperature and humidity of the humidifying chamber outlet.

The temperature sensor at the humidifier end of the delivery hose enables the provision of feedback control of the humidifier outlet gas temperature. The remaining sensor at the patient end provides feedback control of patient gas temperature.

Gas connections 16, 14 are provided that will enable the delivery hose to make gas-tight connection with the outlet with the humidifying chamber and a member in communication with the patient's airway.

What is claimed is:

1. A composite, flexible delivery hose for use with a medical humidifier and having temperature sensors arranged one at each end of the hose, said hose comprising an inner flexible tubular member and a heater cable attached to and wound spirally therearound, said heater cable including a first electrical resistance heater wire, a second thermoplastic support wire and a third wire interconnecting said temperature sensors, said first, second and third wires all being imbedded in an outer body of electrically insulating material.

* * * * *